(12) United States Patent
Harper et al.

(10) Patent No.: US 6,540,727 B2
(45) Date of Patent: Apr. 1, 2003

(54) PROCESS FOR TREATING A PATIENT WITH HYDROCEPHALUS UTILIZING AN EXTERNAL MEDICAL DRAINING SYSTEM

(75) Inventors: Derek J. Harper, Santa Ynez, CA (US); Lawrence L. Hampton, Santa Maria, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/874,186

(22) Filed: Jun. 4, 2001

(65) Prior Publication Data
US 2001/0027306 A1 Oct. 4, 2001

Related U.S. Application Data

(63) Continuation-in-part of application No. 09/302,563, filed on Apr. 30, 1999, now Pat. No. 6,277,109.

(51) Int. Cl.[7] .................................................. A61M 1/00
(52) U.S. Cl. ....................... 604/322; 604/540; 604/325; 604/326
(58) Field of Search ................................. 604/540–541, 604/322–323, 325–326, 317–318, 543–544; D24/108, 111, 127–129

(56) References Cited

U.S. PATENT DOCUMENTS

| | | | | |
|---|---|---|---|---|
| 3,957,050 A | * | 5/1976 | Hines, Jr. .................... | 604/118 |
| 4,500,311 A | * | 2/1985 | Redmond et al. ............ | 600/581 |
| 4,621,647 A | * | 11/1986 | Loveland | |
| 4,731,056 A | * | 3/1988 | Tremulis ..................... | 604/118 |
| 5,452,807 A | * | 9/1995 | Foster et al. | |
| 5,772,625 A | * | 6/1998 | Krueger et al. | |
| 5,865,780 A | * | 2/1999 | Tuite ........................... | 602/32 |
| 6,105,912 A | * | 8/2000 | Lindsay et al. ......... | 248/223.41 |
| 2001/0011166 A1 | * | 8/2001 | Harper et al. ............... | 604/322 |

* cited by examiner

Primary Examiner—Michael J. Hayes
Assistant Examiner—Catherine Serke
(74) Attorney, Agent, or Firm—Kelly Bauersfeld Lowry & Kelley, LLP

(57) ABSTRACT

A process for treating a patient with hydrocephalus is disclosed which utilizes an external medical drainage system having a slide interface between a mounting assembly and a disposable drip assembly. The mounting assembly is generally reusable and the drip assembly disposable. The mounting assembly includes a clamp which is fastenable to the pole, and a support rail affixed to the clamp and which has a longitudinal slot that defines an open-face elongated channel. The drip assembly includes a key adjustably positionable within the channel, a graduated cylinder supported by the key, a drainage bag fluidly connected to the graduated cylinder, and tubing extending from the graduated cylinder opposite the drainage bag. A portion of the key disposed within the channel has a cross-sectioned configuration substantially matching the cross section of the channel. The key extends through the slot, but the channel is configured such that the support rail provides means for restricting the key to longitudinal movement within the channel. A lock fixes the key at a desired location within the channel.

31 Claims, 4 Drawing Sheets

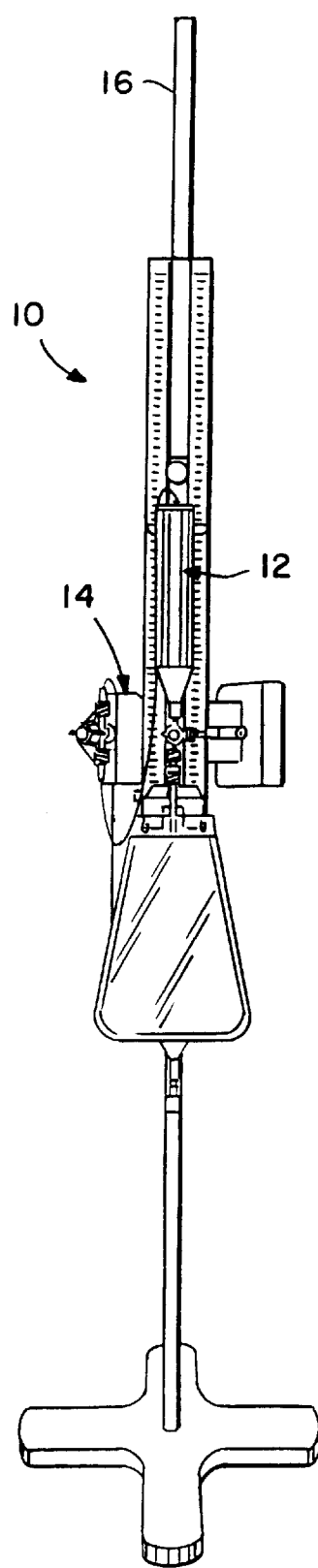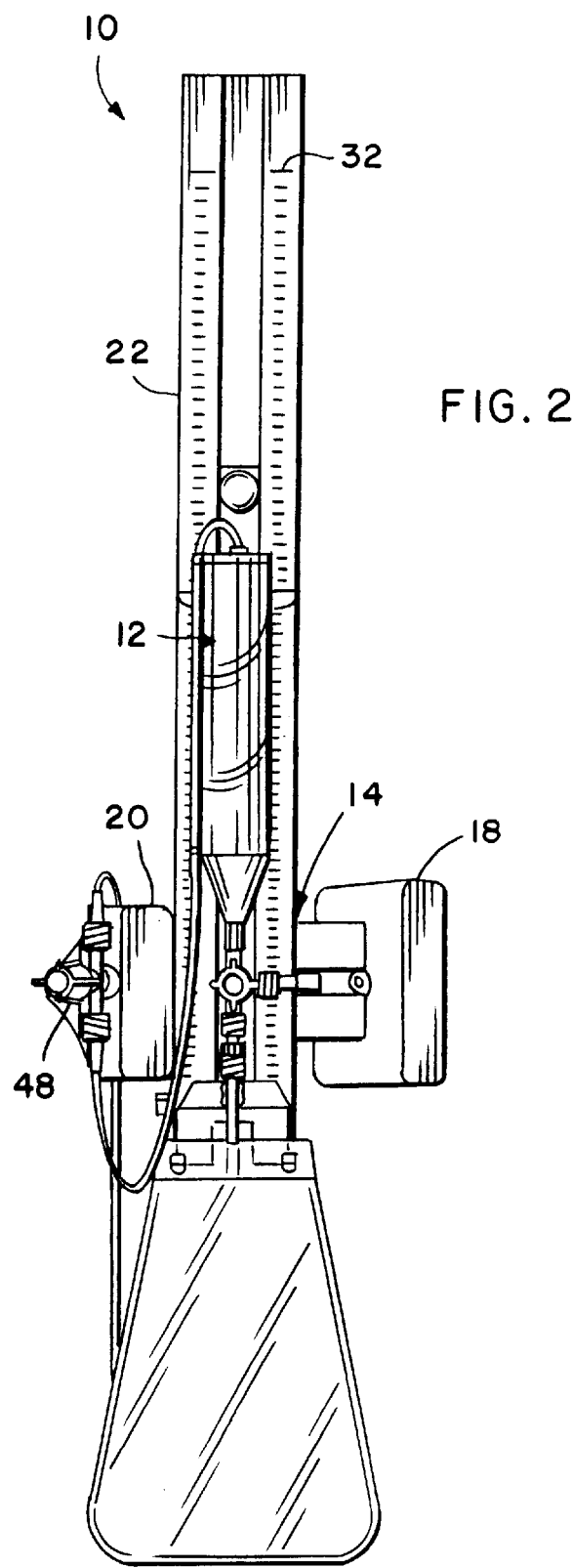

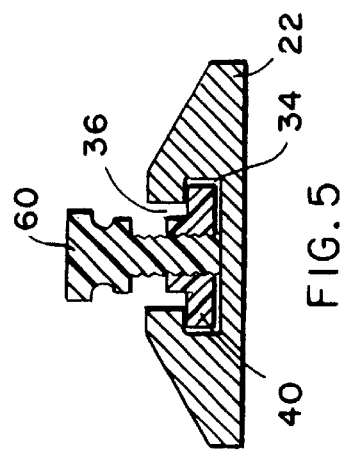
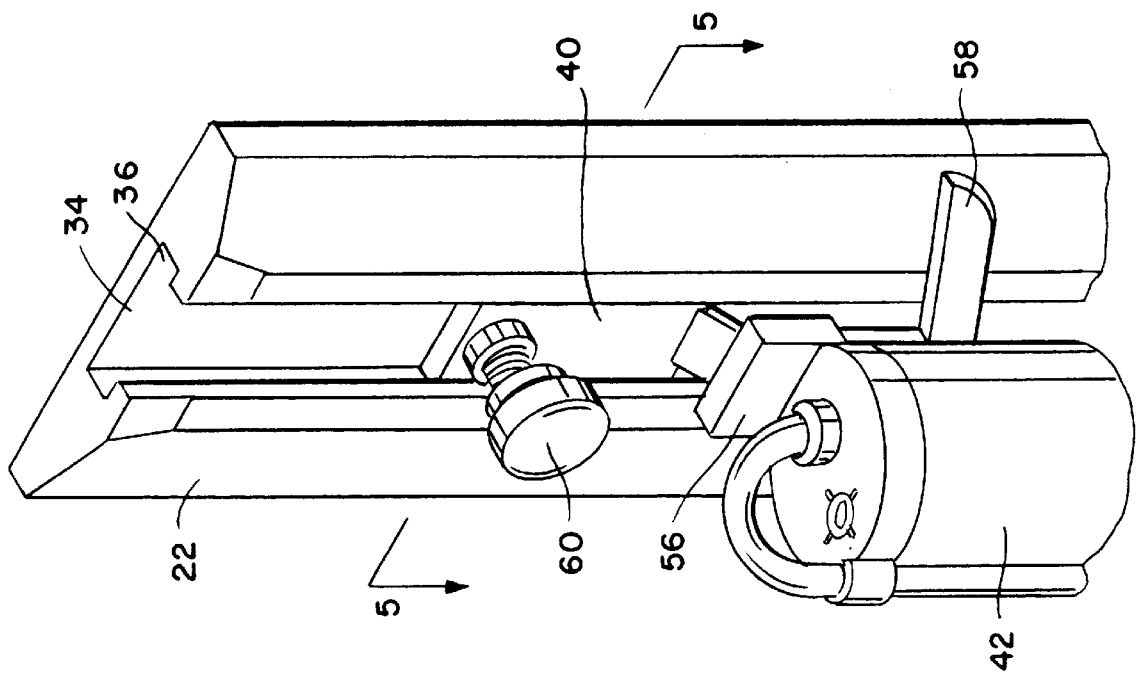

US 6,540,727 B2

PROCESS FOR TREATING A PATIENT WITH HYDROCEPHALUS UTILIZING AN EXTERNAL MEDICAL DRAINING SYSTEM

RELATED APPLICATION

This application is a continuation-in-part of U.S. patent application Ser. No. 09/302,563 filed Apr. 30, 1999 now U.S. Pat. No. 6,277,109 for EXTERNAL MEDICAL DRAINAGE SYSTEM HAVING A SLIDE INTERFACE BETWEEN MOUNTING AND DRIP ASSEMBLIES.

BACKGROUND OF THE INVENTION

The present invention relates generally to external medical drainage systems. More particularly, the present invention relates to a process for treating a patient with hydrocephalus utilizing a medical drainage system having a slide interface between a mounting assembly and a disposable drip assembly.

As is well known in the medical arts, to relieve an undesirable accumulation of fluids from a part of the body it is frequently necessary to provide a means for draining the fluid away from the body. Such is the case, for example, in the treatment of hydrocephalus, an ailment usually afflicting infants or children in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain either to another part of the body or to an external source. External drainage systems typically are attached to IV poles and include a mounting assembly having a pole clamp and a scale, and a drip assembly adjustably fastened to the mounting assembly. The drip assembly typically includes a fluid-receiving graduated cylinder which often empties into a disposable bag.

A zero reference point on the skull is usually found using a laser level or other means. A zero point on the scale is aligned with this zero reference point on the skull. A zero reference stopcock having fluid valves is also aligned with the zero reference point and usually attached to the pole clamp. In order to control the flow of cerebrospinal fluid and maintain the proper pressure in the brain ventricle, the drip assembly is elevated or lowered along the scale to encourage or reduce a gravity or pressure flow from the brain ventricles into the cylinder and/or bag.

Although many such devices have been used in the past, they all have shortcomings. In some drainage systems all of the components of the mounting assembly and drip assembly are disposable. This undesirably increases the amount of hospital waste generated. Other drainage systems utilize reusable mounting assemblies with disposable drip assemblies. However, the drip assemblies on these systems are oftentimes loosely fitted to the scale resulting in the lateral movement and rotation of the cylinder about the point of attachment. This movement can cause inaccurate readings of fluid collected. Such prior systems also inconveniently require two hands to attach the zero reference stopcock to the mounting assembly. Moreover, the configuration and design of these systems makes it difficult to accurately read pressure markings on the scale.

Therefore, what is needed is an external drainage system wherein the zero reference stopcock conveniently attaches to the mounting assembly, and wherein the drip assembly is securely attached to and easily movable along the scale. The present invention fulfills these needs and provides other related advantages.

SUMMARY OF THE INVENTION

The present invention resides in a process for treating a patient with hydrocephalus utilizing an external medical drainage system having a slide interface between the mounting and drip assemblies, and a stopcock mounting clip that snap-fits to the mounting assembly, wherein the mounting assembly is attachable to an IV pole and the drip assembly fastens to the mounting assembly. The mounting assembly includes a clamp which is fastenable to the pole and a support rail affixed to the clamp. The support rail has a longitudinal slot which defines an open-face elongated channel. The clamp and support rail of the mounting assembly are typically reusable. The drip assembly includes a key adjustably positionable within the channel, a graduated cylinder supported by the key, a drainage bag fluidly connected to the graduated cylinder, tubing extending from the graduated cylinder opposite the drainage bag, and a stopcock associated with the tubing and snap-fit to the clamp. The drip assembly is preferably disposable.

The clamp includes a flange having a pair of clip-accepting notches. The clip itself includes a pair of resiliently flexible fingers which extend outwardly from the stopcock and are configured to engage the clamp at the clip-accepting notches such that the clip snap-fits to the clamp of the mounting assembly.

The cross section of the channel is wider interiorly of the support rail than that of the slot. A portion of the key disposed within the channel has a cross-sectional configuration substantially matching the cross section of the channel. The key extends through the slot, but the channel is configured such that the support rail provides means for restricting the key to longitudinal movement within the channel. A lock fixes the key at a desired location within the channel. The lock comprises a screw which is threadable through the key, coming into frictional contact with the support rail within the channel.

In use, the clamp of the mounting assembly is fastened to the pole and the support rail fixed to the clamp. The resiliently flexible fingers of the stopcock clip are fitted over the notches of the clamp, resulting in the clip being snap-fitted to the clamp. The key of the drip assembly is inserted into the channel and slidably positioned to a desired location along the support rail. The drip assembly is fastened to the support rail by turning the screw through the key and channel and into contact with the support rail. The drip assembly is repositioned by turning the screw to release it from contact with the support rail and repositioning the drip assembly.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an elevational view of the external medical drainage system of the present invention fastened to a pole;

FIG. 2 is an enlarged elevational view of the external medical drainage system of FIG. 1;

FIG. 4 is a fragmented perspective view of a support rail having an elongated channel and a key of a drip assembly inserted therein;

FIG. 5 is a cross-sectional view along line 5—5 of FIG. 4, illustrating the key positioned within the channel and a lock screw threaded through the key and into contact with the support rail.

DETAILED DESCRIPTION OF THE PREFERRED EMBODIMENT

Figure 3:
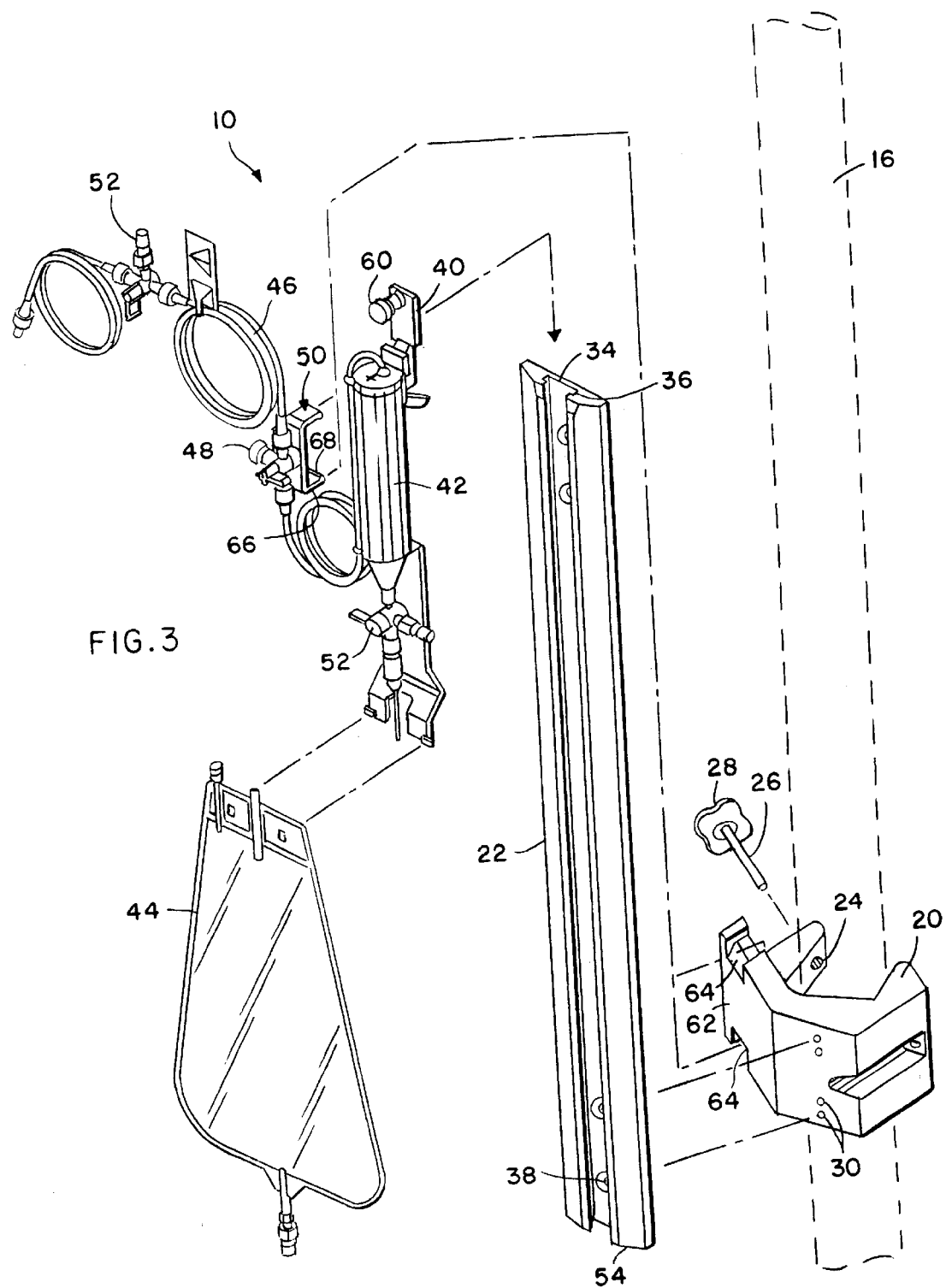
FIG. 3 is an exploded perspective view of the components of the drainage system of FIGS. 1 and 2.

As shown in the drawings for purposes of illustration, the present invention is concerned with a process for treating a patient with hydrocephalus utilizing an external drainage system, generally designated in the accompanying drawings by the reference number 10. The improved drainage system 10 includes a drip assembly 12 fastenable to a mounting assembly 14. The mounting assembly 14 is configured such that it is attachable to a pole 16, such as a hospital IV pole. The external drainage system 10 is intended to be used in situations where there is an undesirable accumulation of fluids in a portion of the body which must be drained from the body. Such is the case in the treatment of hydrocephalus where the ventricles of the brain accumulate excessive fluid. The centroid of the ventricular system, or foramen of Monro, is found and a catheter inserted at this point (not shown). The drainage system 10 is aligned with the catheter insertion point using a laser leveling device 18 attached to the mounting assembly 14 or other adequate means. Fluid is then controllably drained from the brain ventricles to a storage or disposal site outside the body.

With reference to FIGS. 1–3, the mounting assembly 14 is reusable and generally comprises a reusable clamp 20 fastenable to the pole 16 and a support rail 22 fixed to the clamp 20. The clamp 20 includes a threaded aperture 24 and a bolt 26 having a knob 28 at one end, which is threadedly inserted through the aperture 24 and into frictional contact with the pole 16. The clamp 20 also includes additional apertures 30 through which are inserted fasteners such as pins or flat head screws (not shown) for the fixation of the support rail 22 to the clamp 20.

The support rail 22 includes graduated markings 32 which indicate levels of pressure, typically in millimeters mercury (mm Hg) and centimeters water (cm $H_2O$). The markings 32 may be color-coded or of different colors to more easily differentiate the two pressure systems. The support rail 22 also forms an elongated channel 34 and a longitudinal slot 36 which defines the open-face portion of the channel 34. As best viewed in FIGS. 4 and 5, the channel 34, in cross section, is wider within the support rail 22 than the width of the slot 36. The support rail 22 also includes apertures 38 which are aligned with the apertures 30 of the clamp and through which are inserted the fasteners for fixing the support rail 22 to the clamp 20.

The drip assembly 12 is disposable and generally comprises a key 40 at least partially insertable into the open-face channel 34, a graduated cylinder 42 supported by the key 40, a drainage bag 44 fluidly connected to the graduated cylinder 42, tubing 46 extending from the graduated cylinder 42 opposite the drainage bag 44, and a zero reference stopcock 48 associated with the tubing 46 and fixed to a clip 50. The drip assembly 12 may include additional sections of tubing 46 as may be necessary to connect the drip assembly 12 to a drainage catheter and may also include additional stopcocks 52, usually between the sections of tubing 46 and also between the graduated cylinder 42 and the drainage bag 44, in order to reduce or shut off the flow of fluid from one section of the drip assembly 12 to another.

Referring to FIGS. 4 and 5, the key 40 is insertable into the channel 34. At least a portion of the key 40 has a cross-sectional configuration substantially matching that of the channel 34. Due to the fact that the cross section of the channel 34 is wider than the slot 36, the key 40 moves in a longitudinal direction only. The key 40 is preferably manufactured of a sufficient length so as to provide adequate support to the drip assembly 12. In this regard, the longer the key 40, the more stabilization and support given to the drip assembly 12 hanging from the support rail 22. The key 40 may include member 56 for removable attachment to the cylinder 42, and/or wings 58 which aid the provider in reading the markings 32. The key 40 also includes a lock 60 which comprises a screw threadable through the key 40 and into frictional contact with the support rail 22 within the channel 34. The lock 60 extends out from the slot 36 so as to be accessible to the medical care provider adjusting the drip assembly 12.

Figure 6:
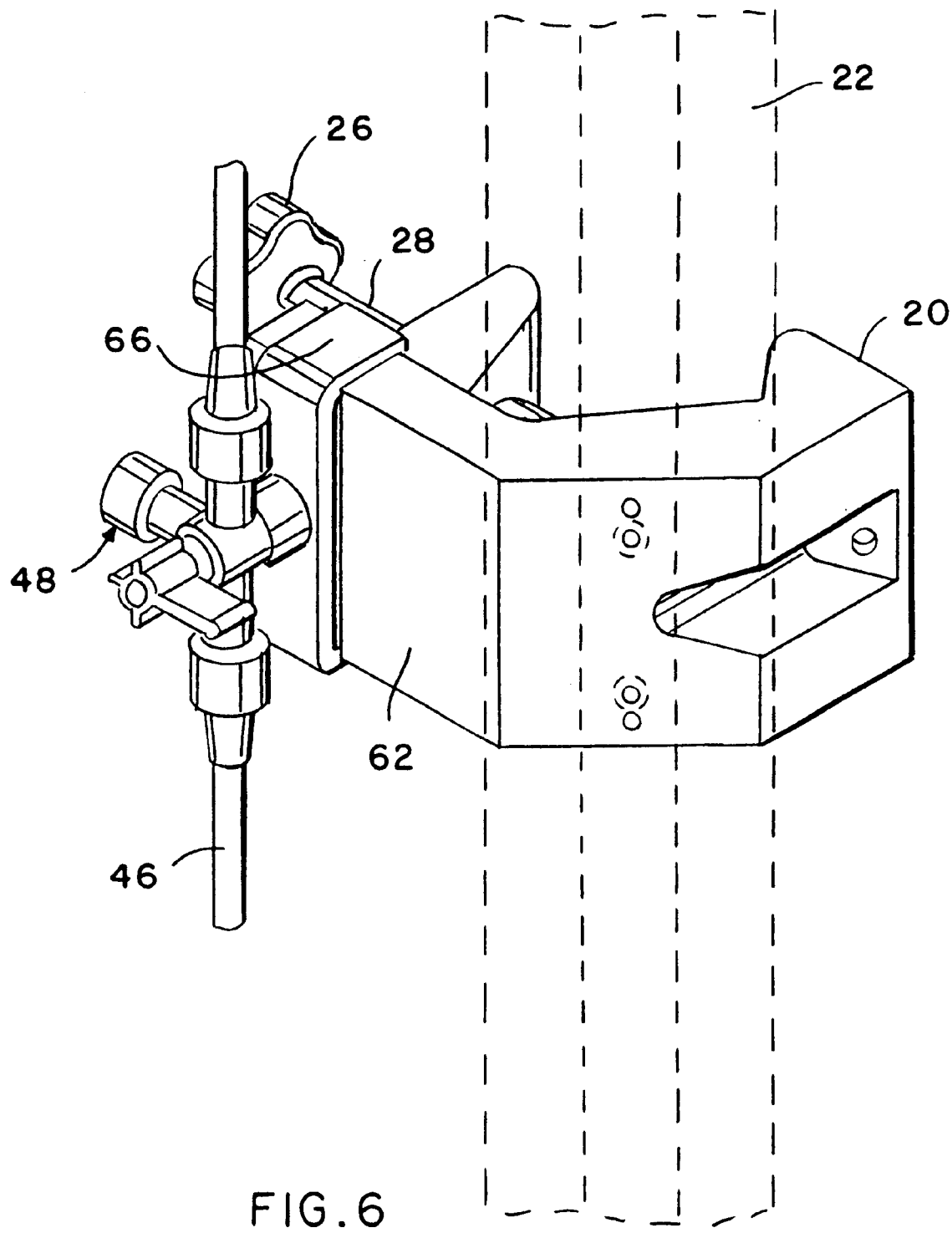
FIG. 6 is a partial perspective view of a clamp attachable to the pole having a snap-fit clip attached to one portion thereof and the support rail (in phantom) attached to another portion thereof.

As illustrated in FIGS. 3 and 6, the zero reference stopcock 48 and clip 50 are snap-fitted to the clamp 20 at approximately the zero reference marking 32 of the support rail 22. The clip 50 may be configured any number of ways to fit to the clamp 20. In the preferred configuration, the clamp 20 includes a flange 62 having a pair of clip-accepting notches 64. The clip 50 includes a pair of resiliently flexible fingers 66 extending from the stopcock 48 and configured to engage the clamp flange 62 at the notches 64. The fingers 66 of the clip 50 may include cusps 68 or other projections to more securely hold the clip 50 and its associated stopcock 48 to the clamp 20. The design and configuration of the clip 50 and clamp 20 are such that a medical care provider can snap-fit the clip 50 to, or remove the clip 50 from, the clamp 20 using only one hand.

In use, the drainage catheter is placed in the appropriate incision point of the patient. The drainage system 10 is positioned along the pole 16 using the laser leveling device 18 or other appropriate leveling means and the mounting assembly 14 is fastened to the pole 16 by turning the knob 28 until the bolt 26 contacts the pole 16 to frictionally hold the clamp 20 in place. If the support rail 22 is not already fixed to the clamp 20, its apertures 38 are aligned with the apertures 30 of the clamp 20 and fasteners are inserted through the rail 22 and into the clamp 20.

The key 40 is inserted into the channel 34 and moved into a desired position and the lock 60 secured to the support rail 22 to hold the key 40 and other components of the drip assembly 12 in place. The drip assembly 12 may be repositioned by loosening the lock 60 and slidingly repositioning the key 40 and resecuring the lock 60, by turning the threaded screw through the key 40. The tubing 46 is connected to the drainage catheter and the stopcocks opened to allow the fluid to drain away from the body. The flow of fluid is controlled by the opening and closing of the stopcocks 48 and 52, and by the position of the drip assembly 12 along the channel 34. Raising the drip assembly 12 slows the flow of fluid, and lowering the assembly 12 increases the flow of fluid.

Although several embodiments have been described in detail for purposes of illustration, various modifications may be made to each without departing from the scope and spirit of the invention. Accordingly, the invention is not to be limited, except as by the appended claims.

What is claimed is:

1. A process for treating a patient with hydrocephalus, comprising the steps of:
   attaching an adjustably positionable pole mounting assembly to a pole adjacent to the patient, the pole mounting assembly having an elongated channel and a longitudinal slot which defines an open-face of the channel, and clamp adjustably fastenable to the pole, and a support rail fixed to the clamp and which forms the elongated channel;
   attaching a zero reference stopcock fluidly connected to the disposable drainage assembly, to the clamp;
   slidably mounting a disposable drip assembly to the pole mounting assembly;
   inserting a catheter into a ventricular system of the patient and fluidly connecting the catheter to the disposable drip assembly;
   positioning the pole mounting assembly and disposable drip assembly to a predetermined position relative to the catheter; and
   controllably draining fluid from the patient's ventricular system to the disposable drip assembly.

2. The process of claim 1, wherein the pole mounting assembly includes a clamp adjustably fastenable to the pole, and a support rail fixed to the clamp and which forms the elongated channel.

3. The process of claim 2, including the step of attaching a zero reference stopcock fluidly connected to the disposable drainage assembly, to the clamp.

4. The process of claim 1, wherein the attaching step comprises inserting a bolt through an aperture of the clamp and into contact with the pole.

5. The process of claim 4, wherein the bolt includes a knob which facilitates the release and tightening of the bolt so that the pole mounting assembly and disposable drip assembly can be repositioned with one hand.

6. The process of claim 1, wherein the mounting step includes the step of inserting a key extending from a disposable drip assembly through the slot and into the channel of the pole mounting assembly such that the disposable drip assembly is slidably positionable along the length of the channel.

7. The process of claim 1, wherein the positioning step includes substantially aligning the pole mounting assembly with the catheter using a leveling device associated with the pole mounting assembly.

8. The process of claim 7, wherein the leveling device comprises a laser.

9. A process for treating a patient with hydrocephalus, comprising the steps of:
   attaching an adjustably positionable pole mounting assembly to a pole adjacent to the patient, the pole mounting assembly including a clamp adjustably fastenable to the pole, and a support rail fixed to the clamp and which forms an elongated channel and a longitudinal slot which defines an open-face of the channel;
   slidably mounting a disposable drip assembly to the pole mounting assembly by inserting a key extending from a disposable drip assembly through the slot and into the channel of the pole mounting assembly such that the disposable drip assembly is slidably positionable along the length of the channel;
   inserting a catheter into a ventricular system of the patient and fluidly connecting the catheter to the disposable drip assembly;
   substantially aligning the pole mounting assembly with the catheter and positioning the disposable drip assembly to a predetermined position along the channel; and
   controllably draining fluid from the patient's ventricular system to the disposable drip assembly.

10. The process of claim 9, wherein the attaching step comprises inserting a bolt through an aperture of the clamp and into contact with the pole.

11. The process of claim 10, wherein the bolt includes a knob which facilitates the release and tightening of the bolt so that the pole mounting assembly and disposable drip assembly can be repositioned with one hand.

12. The process of claim 9, including the step of attaching a zero reference stopcock fluidly connected to the disposable drainage assembly, to the clamp.

13. The process of claim 9, wherein the key of the disposable drainage assembly has a cross-sectional configuration substantially matching that of the channel such that it is limited to longitudinal travel within the channel.

14. The process of claim 9, wherein the disposable drainage assembly includes a screw threadable through the key and into frictional contact with the pole mounting assembly within the channel to fix the disposable drip assembly in place along the length of the channel.

15. The process of claim 14, wherein the screw extends from the slot and is configured to be loosened and tightened and the disposable drip assembly moved along the length of the channel with one hand.

16. The process of claim 9, wherein the disposable drainage assembly includes a graduated cylinder supported by the key, a drainage bag fluidly connected to the graduated cylinder, and tubing extending from the graduated cylinder opposite the drainage bag.

17. The process of claim 9, wherein the aligning step includes using a leveling device to substantially align the pole mounting assembly with the catheter.

18. The process of claim 17, wherein the leveling device comprises a laser.

19. A process for treating a patient with hydrocephalus, comprising the steps of:
   attaching an adjustably positionable pole mounting assembly to a pole adjacent to the patient, the pole mounting assembly including a clamp adjustably fastenable to the pole, and a support rail fixed to the clamp and which forms an elongated channel and a longitudinal slot which defines an open-face of the channel;
   slidably mounting a disposable drip assembly to the pole mounting assembly by inserting a key extending from a disposable drip assembly through the slot and into the channel of the pole mounting assembly such that the disposable drip assembly is slidably positionable along the length of the channel, wherein the disposable drainage assembly includes a screw threadable through the key and into frictional contact with the pole mounting assembly within the channel to fix the disposable drip assembly in place along the length of the channel, the screw extending from the slot and being configured to be loosened and tightened and the disposable drip assembly moved along the length of the channel with one hand;
   attaching a zero reference stopcock fluidly connected to the disposable drainage assembly, to the clamp;
   inserting a catheter into a ventricular system of the patient and fluidly connecting the catheter to the disposable drip assembly;
   substantially aligning the zero reference stopcock with the catheter and positioning the disposable drip assembly to a predetermined position along the channel; and controllably draining fluid from the patient's ventricular system to the disposable drip assembly.

20. The process of claim 19, wherein the attaching step comprises inserting a bolt through an aperture of the clamp and into contact with the pole.

21. The process of claim 20, wherein the bolt includes a knob which facilitates the release and tightening of the bolt so that the pole mounting assembly and disposable drip assembly can be repositioned with one hand.

22. The process of claim 19, wherein the key of the disposable drainage assembly has a cross-sectional configuration substantially matching that of the channel such that it is limited to longitudinal travel within the channel.

23. The process of claim 19, wherein the disposable drainage assembly includes a graduated cylinder supported by the key, a drainage bag fluidly connected to the graduated cylinder, and tubing extending from the graduated cylinder opposite the drainage bag.

24. The process of claim 19, wherein the aligning step includes using a leveling device to substantially align the pole mounting assembly with the catheter.

25. The process of claim 24, wherein the leveling device comprises a laser.

26. A process for treating a patient with hydrocephalus, comprising the steps of:
    attaching an adjustably positionable pole mounting assembly to a pole adjacent to the patient, the pole mounting assembly having an elongated channel and a longitudinal slot which defines an open-face of the channel;
    slidably mounting a disposable drip assembly to the pole mounting assembly;
    inserting a catheter into a ventricular system of the patient and fluidly connecting the catheter to the disposable drip assembly;
    positioning the pole mounting assembly and disposable drip assembly to a predetermined position relative to the catheter; and
    controllably draining fluid from the patient's ventricular system to the disposable drip assembly;
    wherein the mounting step includes the step of inserting a key extending from the disposable drip assembly through the slot and into the channel of the pole mounting assembly such that the disposable drip assembly is slidably positionable along the length of the channel.

27. The process of claim 26, wherein the key of the disposable drainage assembly has a cross-sectional configuration substantially matching that of the channel such that it is limited to longitudinal travel within the channel.

28. The process of claim 26, wherein the disposable drainage assembly includes a screw threadable through the key and into frictional contact with the pole mounting assembly within the channel to fix the disposable drip assembly in place along the length of the channel.

29. The process of claim 28, wherein the screw extends from the slot and is configured to be loosened and tightened and the disposable drip assembly moved along the length of the channel with one hand.

30. The process of claim 26, wherein the disposable drainage assembly includes a graduated cylinder supported by the key, a drainage bag fluidly connected to the graduated cylinder, and tubing extending from the graduated cylinder opposite the drainage bag.

31. A process for treating a patient with hydrocephalus, comprising the steps of:
    attaching an adjustably positionable pole mounting assembly to a pole adjacent to the patient, the pole mounting assembly having an elongated channel and a longitudinal slot which defines an open-face of the channel;
    slidably mounting a disposable drip assembly to the pole mounting assembly and inserting a key extending from the disposable drip assembly through the slot and into the channel of the pole mounting assembly such that the disposable drip assembly is slidably positionable along the length of the channel;
    inserting a catheter into a ventricular system of the patient and fluidly connecting the catheter to the disposable drip assembly;
    positioning the pole mounting assembly and disposable drip assembly to a predetermined position relative to the catheter; and
    controllably draining fluid from the patient's ventricular system to the disposable drip assembly;
    wherein the positioning step includes substantially aligning the pole mounting assembly with the catheter using a laser leveling device associated with the pole mounting assembly.

* * * * *